US00PP23163P2

(12) United States Plant Patent
Zylstra

(10) Patent No.: US PP23,163 P2
(45) Date of Patent: Nov. 6, 2012

(54) ***MYOPORUM* PLANT NAMED 'CLEAN N GREEN'**

(50) Latin Name: *Myoporum laetum*
Varietal Denomination: CLEAN n GREEN

(76) Inventor: Doug Zylstra, Santa Barbara, CA (US)

( * ) Notice: Subject to any disclaimer, the term of this patent is extended or adjusted under 35 U.S.C. 154(b) by 103 days.

(21) Appl. No.: 12/925,230

(22) Filed: Oct. 18, 2010

Related U.S. Application Data

(60) Provisional application No. 61/281,201, filed on Nov. 16, 2009.

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell

(57) ABSTRACT

A new cultivar of *Myoporum laetum* named 'CLEAN n GREEN' which does not exhibit symptoms of attack by thrips, which are leaf-feeding insect pests which commonly affects plants and plantings of *Myoporum laetum*. 'CLEAN n GREEN' exhibits healthy green, glossy and perfectly shaped foliage. In combination with its upright form and well-branching habit, these characteristics distinguish 'CLEAN n GREEN' from all other existing varieties of *Myoporum* known to the inventor.

3 Drawing Sheets

Genus: *Myoporum.*
Species: *laetum.*
Denomination: 'CLEAN n GREEN'.

BACKGROUND OF THE INVENTION

The present invention relates to a new and distinct cultivar of *Myoporum*, which is grown as an ornamental shrub for use in the garden and landscape. The new cultivar is known botanically as *Myoporum laetum*, and will be referred to hereinafter by the cultivar name 'CLEAN n GREEN'.

'CLEAN n GREEN' was discovered by the inventor in 2009 as a naturally occurring single whole plant mutation which the inventor had observed in an established cultivated hedge planting consisting of many plants of *Myporum laetum* (species, unpatented) in Santa Barbara, Calif. The inventor observed that 'CLEAN n GREEN' did not exhibit any of the symptoms of attack by thrips, which are leaf-feeding insect pests which commonly affects plants and plantings of *Myoporum laetum*. Whereas, neighboring and even adjacent plants of *Myporum laetum* all exhibited the leaf deformity which is characteristic of thrip attack, the single plant of 'CLEAN n GREEN' was entirely free of such symptoms, and exhibited healthy green, glossy and perfectly shaped foliage.

'CLEAN n GREEN' was first asexually propagated by the inventor in June 2009 in Santa Barbara, Calif. Asexual propagation was accomplished using semi-hardwood cuttings. The inventor continued to observe the discovered plant 'CLEAN n GREEN' and has observed the plants which have been asexually propagated from 'CLEAN n GREEN'. Both the original plant and all subsequent plants have remained unaffected by thrip attack despite being deliberately exposed to insect pressure from other infested plants which the inventor placed in close proximity.

The inventor has determined that the distinguishing characteristic of 'CLEAN n GREEN', namely resistance to attack by thrips, has remained present in subsequent generations, and that in all respects 'CLEAN n GREEN' reproduces true to type in successive generations of asexual propagation.

BRIEF DESCRIPTION OF THE INVENTION

The distinguishing characteristics of 'CLEAN n GREEN' are as follows: In combination these traits set 'CLEAN n GREEN' apart from all other existing varieties of *Myoporum* known to the inventor. 'CLEAN n GREEN' has not been tested under all possible conditions and phenotypic differences may be observed with variations in environmental, climatic, and cultural conditions. All growth descriptions are for plants which have been grown out of doors in Santa Barbara, Calif.

1. 'CLEAN n GREEN' naturally well-branching at the base and along the stems, making it highly suitable for use as a hedging plant.
2. The foliage of 'CLEAN n GREEN' is glossy and pale green when juvenile, and glossy and mid green when mature.
3. 'CLEAN n GREEN' is resistant to infestation by thrips.
4. In its first season of growth when planted in the landscape, 'CLEAN n GREEN' achieves a height of 1.2 meters and a width of 1.2 meters.
5. When planted in the landscape and mature, a plant of 'CLEAN n GREEN' achieves a height of approximately 6.0-6.2 meters and a spread of approximately 6.0 meters.
6. 'CLEAN n GREEN' is hardy to 30 degrees Fahrenheit and, as is typical of the species parent, will thrive in Sunset Western Climate Zones 8, 9, 14-17 and 19-24.

DESCRIPTION OF THE DRAWINGS

The accompanying color drawings illustrate the overall appearance of 'CLEAN n GREEN' showing the colors of its foliage and flowers as true as it is reasonably possible to obtain in colored reproductions of this type.

The drawing labeled

Figure 1:
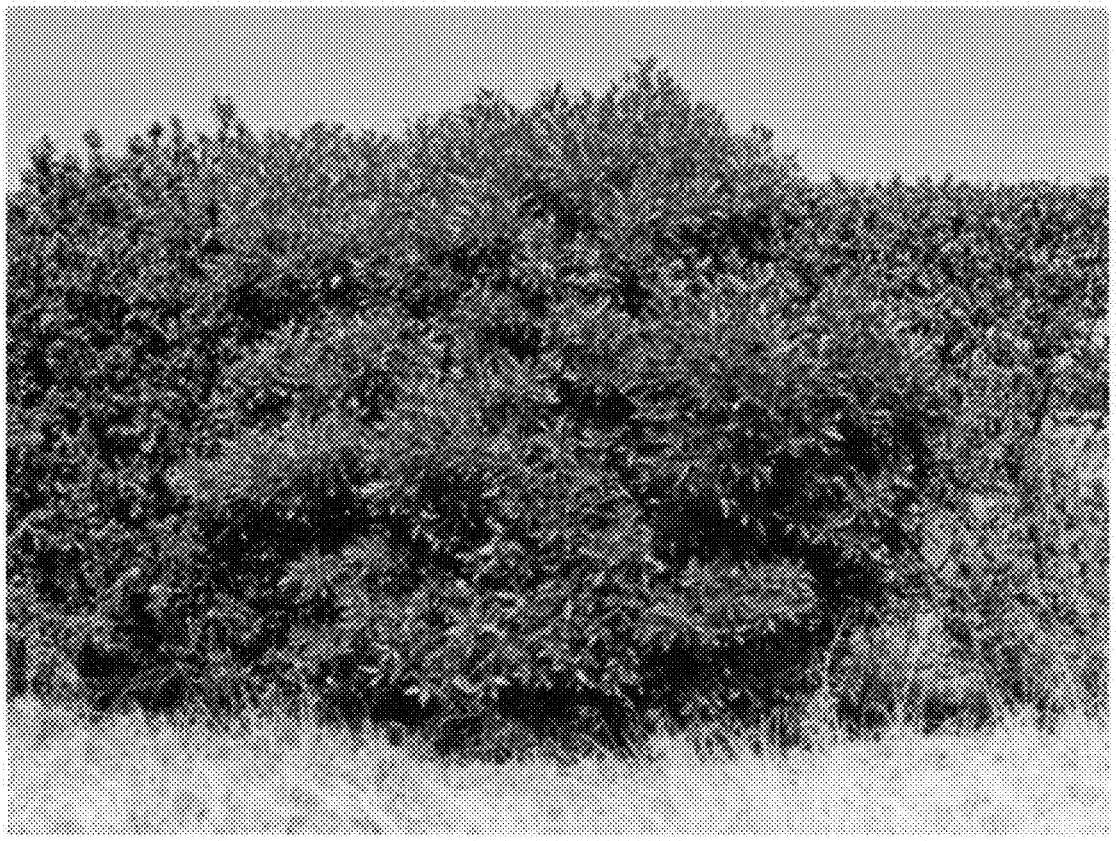
FIG. 1 shows the original discovered plant of 'CLEAN n GREEN' which is still in situ in the landscape planting in Santa Barbara, Calif. Whereas the plant of 'CLEAN n GREEN' appears healthy and full, the adjacent and nearby plants of *Myoporum laetum* are evidently severely affected by thrip attack.
Figure 2:
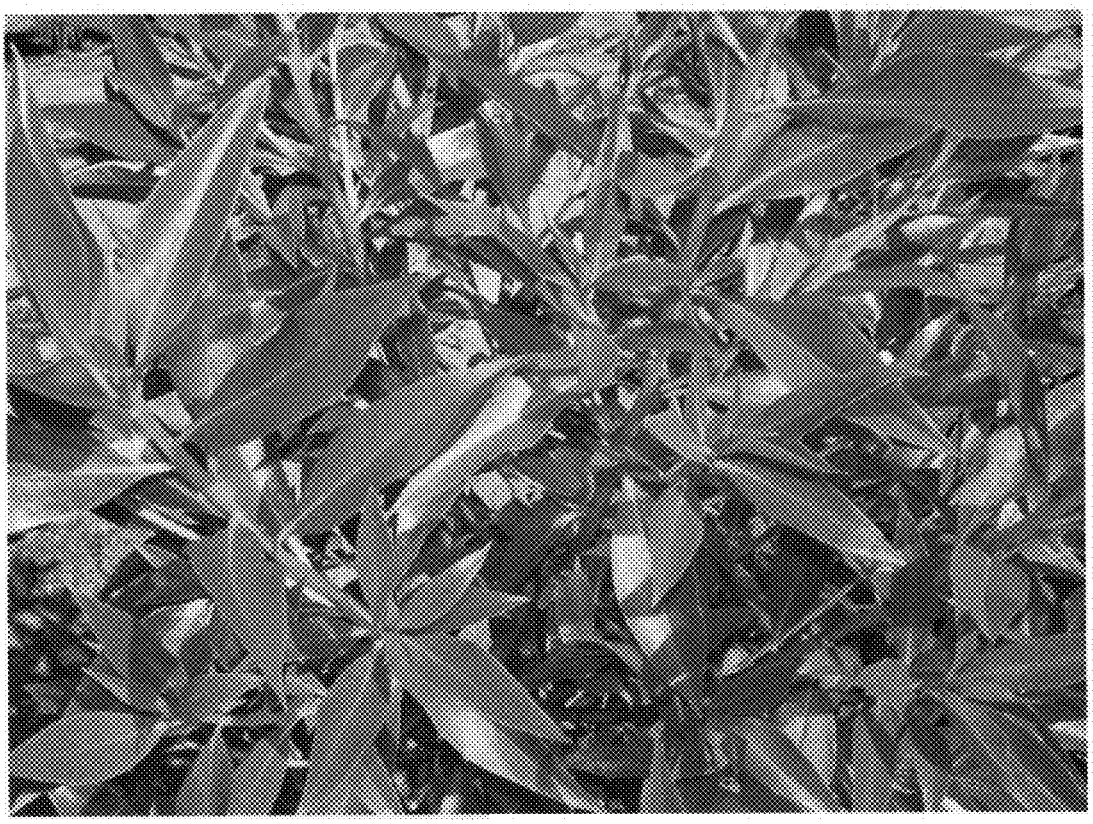

The drawing labeled as FIG. 2 shows the foliage of a plant of 'CLEAN n GREEN' which has been asexually propagated from the original discovered plant. The foliage is entirely free of any symptoms of attack by thrips and appears glossy and healthy despite having been positioned in close proximity to plants which were infested with thrips.

Figure 3:
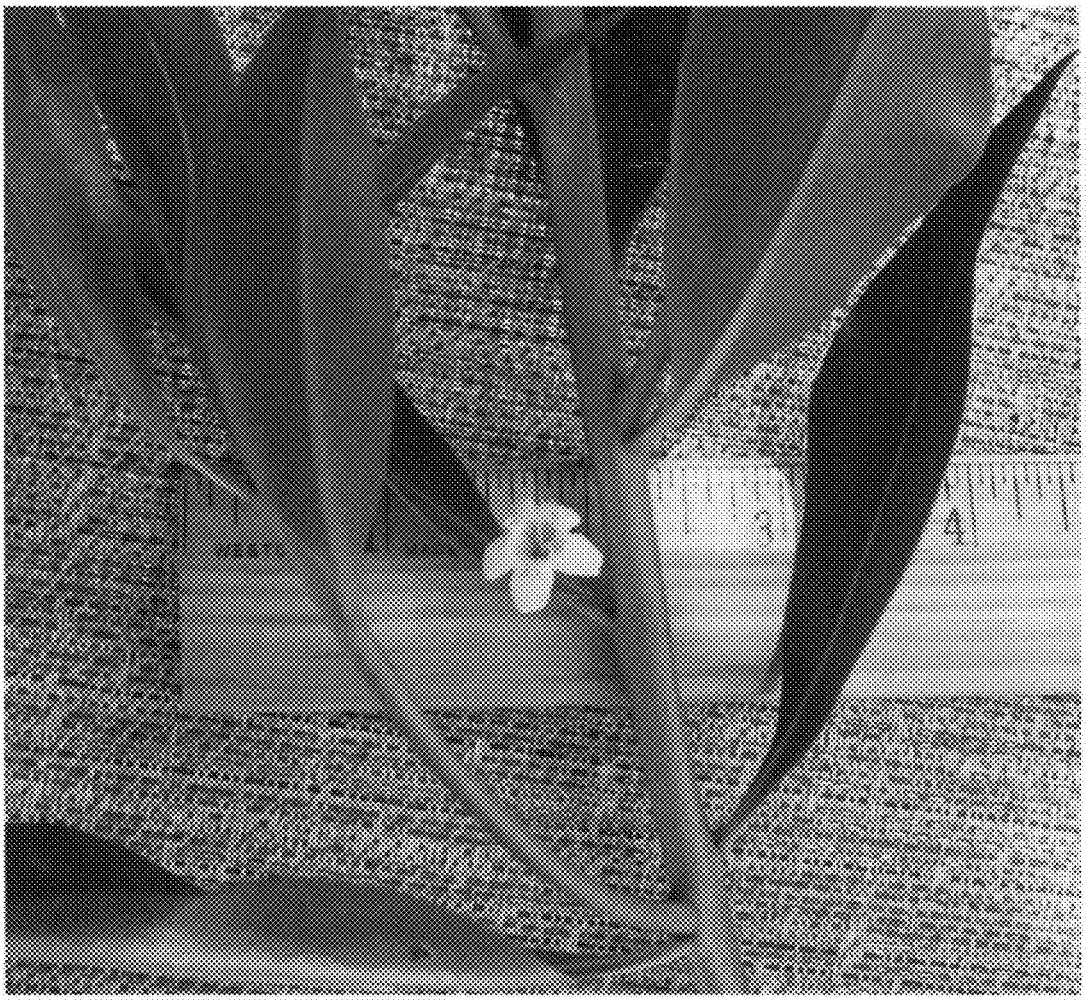

The drawing labeled as FIG. 3 shows a solitary flower of 'CLEAN n GREEN'.

BOTANICAL DESCRIPTION OF THE PLANT

The following is a detailed description of the *Myoporum laetum* cultivar named 'CLEAN n GREEN'. Data was collected from an eighteen months old plant growing out of doors in a 3 gallon container in Santa Barbara, Calif. When grown entirely in a container, the height and spread of 'CLEAN n GREEN' are reduced as described herein. The observed plant had been pruned down to 10 cm above soil level in order to encourage basal and lateral branching as would be typical of commercial cultural practice. Color determinations are in accordance with The Royal Horticultural Society Colour Chart, 2007 Edition, except where general color terms of ordinary dictionary significance are used.

Botanical classification: *Myoporum laetum* 'CLEAN n GREEN'.

Use: Ornamental landscape and hedging plant.

Parent: 'CLEAN n GREEN' arose as a naturally occurring whole plant sport which was observed within an established hedge planting of many plants of the species *Myoporum laetum* (unpatented).

Type: Evergreen shrub.

Vigor: Medium.

Habit: Upright.

Dimensions: Height: 85 cm; width: 80 cm.

Hardiness: USDA Zone 9.

Propagation: Medium hardwood cuttings.

Root system: Coarse surface roots and dense fibrous root system throughout the container.

Soil: Plant in loam or well drained soil.

Sunlight: Plant in full sunlight.

Diseases and pests: Resistant to thrips and not susceptible to any other pests or diseases known to the inventor.

Stems:

*Branching habit*.—Prolific. Branches are strong and wiry and quickly turn upright.

*Number of branches*.—After pruning the apical shoot at 10 cm above the soil level, seven branches resulted below. Numerous lateral branches emerge from each of these basal branches. Lateral branching is axillary and occurs at each node.

*Basal branches*.—Length 75 cm, diameter 7 mm-10 mm.

*Lateral branches*.—Length 10 cm-30 cm; diameter 5 mm-8 mm.

*Internode length* (*all branches*).—2 cm-3 cm.

*Shape*.—Irregular quadrangular.

*Stem surface* (*lignified, mature*).—Rough, coriaceous, color ranges between 161A and 163D.

*Stem surface* (*green, juvenile*).—Slightly rough with numerous rounded lenticels which are readily felt but barely discernable. Color (including lenticels) 138B.

*Stem surface color at each node and extending approximately* 0.5 *cm on either side of each node*.—173B.

*Pubescence*.—Absent.

Foliage:

*Leaf arrangement*.—Alternate.

*Leaf division*.—Simple.

*Leaf number per basal branch*.—30-40.

*Leaf number per lateral branch*.—8-20.

*Leaf shape*.—Lanceolate.

*Leaf base*.—Acuminate.

*Leaf apex*.—Markedly acuminate.

*Leaf venation*.—Pinnate, with prominent mid vein; other veins barely discernable, appears pinnate.

*Vein color* (*both surfaces*).—Mid vein N144D; other veins as leaf lamina.

*Pubescence*.—None present.

*Margin*.—Entire, smooth.

*Leaf surface* (*both surfaces*).—Smooth, with numerous raised oil glands which appear as tiny dots. Each gland has diameter less than 0.5 mm and is raised less than 0.25 mm. Glands are approximately 1 mm apart and are present throughout both leaf surfaces. Gland color is 145C.

*Leaf attachment*.—Petiolate.

*Petiole length*.—8 mm-12 mm.

*Petiole shape*.—Flattened: width 2.5 mm, depth 1.5 mm.

*Petiole color*.—N144D.

*Petiole surface*.—Smooth.

*Leaf dimensions*.—3.5 cm in width and 10 cm in length.

*Leaf color*.—Upper surface 141A; lower 138A.

Flowers: Flowers appear to be mostly absent. Where observed, flowers are axillary and occur singly or in pairs or in groups of four to six flowers.

*Arrangement*.—Solitary. When present as two or more flowers in an axillary group, each flower and its peduncle is solitary.

*Peduncles*.—Attachment: Axillary and (if more than one flower in the axillary group) adjacent to others without joining at base. Dimensions: Length 8 mm-12 mm; diameter 1 mm. Color: 143C.

*Corolla*.—Shape: Stellar, sympetalous, five lobes slightly recurving. Diameter: 18 mm. Depth: 5 mm. Lobe apex: Rounded. Lobe base: Truncate. Lobe margin: Smooth, entire. Texture (upper surface): Wax-like, glossy, pubescent except at margins. Hairs tiny, very fine, 2 mm in length, color appears gray-white. Texture (lower surface): Wax like, smooth, glossy. Color (upper surface): NN155D with two to four longitudinal rows of purple-gray spots numbering from 16 to approximately 40 on each lobe. Spots commence at 5 mm from lobe apex and extend to lobe base. Spots are irregularly shaped, typically round to slightly elliptic. Spot diameter varies between 0.5 mm and 1.0 mm, Spots are not raised. Spot color N187A.

*Reproductive organs*.—Stamens: 4 in number, exserted, 5 mm-7 mm in length, color white. Anthers: Elliptic, 2.5 mm in length, 1.5 mm in diameter, color 157D. Fruit: Not observed. To date, all flowers have aborted.

The invention claimed is:

1. A new and distinct variety of *Myoporum laetum* plant named 'CLEAN n GREEN' as described and illustrated.

* * * * *